(12) United States Patent
Piri et al.

(10) Patent No.: US 10,302,540 B2
(45) Date of Patent: May 28, 2019

(54) NANOCONDENSATION APPARATUS

(71) Applicant: University of Wyoming, Laramie, WY (US)

(72) Inventors: Mohammad Piri, Laramie, WY (US); Elizabeth Barsotti, Laramie, WY (US); Soheil Saraji, Laramie, WY (US)

(73) Assignee: University of Wyoming, Laramie, WY (US)

( * ) Notice: Subject to any disclaimer, the term of this patent is extended or adjusted under 35 U.S.C. 154(b) by 0 days.

(21) Appl. No.: 15/588,094

(22) Filed: May 5, 2017

(65) Prior Publication Data
US 2018/0321120 A1    Nov. 8, 2018

(51) Int. Cl.
*G01N 5/02* (2006.01)
*G01N 30/06* (2006.01)

(52) U.S. Cl.
CPC .............. *G01N 5/02* (2013.01); *G01N 30/06* (2013.01)

(58) Field of Classification Search
CPC .... G01N 5/02; G01N 30/06; G01N 2030/025; G01N 2203/0005
See application file for complete search history.

(56) References Cited

PUBLICATIONS

Schwartz, R. "Precision determination of adsorption layers on stainless steel mass standards by mass comparison and ellipsometry: Part II: Sorption phenomena in vacuum." Metrologia 31.2 (1994): 129.*
STP1003/1003C Turbomolecular Pump Datasheet. Edwards Limited. 2013. pp. 1-2.*
Gor et al., "Adsorption of n-Pentane on Mesoporous Silica and Adsorbent Deformation", Langmuir, 2013, pp. 8601-8608, vol. 29.
Russo et al., "Trends in the Condensation/ Evaporation and Adsorption Enthalpies of Volatile Organic Compounds on Mesoporous Silica Materials", Microporous and Mesoporous Materials, 2012, pp. 223-230, vol. 151.
Russo et al., "Hydrocarbons Adsorption on Templated Mesoporous Materials: Effect of the Pore Size, Geometry and Surface Chemistry", New Journal of Chemistry, 2011, pp. 407-416, vol. 35.
Qiao et al., "Study of Hexane Adsorption in Nanoporous MCM-41 Silica", Langmuir, 2004, pp. 389-395, vol. 20.
Shim et al., "Heterogeneous Adsorption Characteristics of Volatile Organic Compounds (VOCs) on MCM-48", Separation Science and Technology, 2006, pp. 3693-3719, vol. 41.
Barsotti E. et al. "A Review on Capillary Condensation in Nanoporous Media: Implications for Hydrocarbon Recovery from Tight Reservoirs," Fuel, 2016, pp. 344-361, vol. 184, Elsevier Ltd. (18 pages).
Ioneva M. A. et al. "Capillary Condensation of Light Hydrocarbons in MCM-41—Type Mesoporous Materials" Materials Research Society Symposium Proceedings, 1997, pp. 119-124, vol. 454, Materials Research Society (six (6) pages).

(Continued)

*Primary Examiner* — Daniel S Larkin
(74) *Attorney, Agent, or Firm* — Crowell & Moring LLP

(57) ABSTRACT

The present invention relates to a nanocondensation apparatus comprising a mass comparator, a core holder, an environmental chamber, and a pump and to methods for studying a fluid-solid system with the nanocondensation apparatus.

19 Claims, 8 Drawing Sheets

(56) References Cited

PUBLICATIONS

Casanova F. et al. "Effect of Surface Interactions on the Hysteresis of Capillary Condensation in Nanopores" EPL, 2008, pp. 26003-p1-26003-p5, vol. 81, A Letters Journal Exploring the Frontiers of Physics (five (5) pages).

Morishige K. et al. "Capillary Critical Point of Argon, Nitrogen, Oxygen, Ethylene, and Carbon Dioxide in MCM-41" Langmuir, 1997, pp. 3494-3498, vol. 13, American Chemical Society (five (5) pages).

Zandavi S. H. et al. "Nucleation and Growth of Condensate in Nanoporous Materials" Physical Chemistry Chemical Physics, 2015, pp. 9828-9834, vol. 17, Royal Society of Chemistry (seven (7) pages).

Tanchoux N. et al. "The Adsorption of Hexane over MCM-41 Type Materials" Colloids and Surfaces A: Physicochemical Engineering Aspects, 2004, pp. 1-8, vol. 246, Elsevier Ltd. (eight (8) pages).

Chen J. et al. "Capillary Condensation and NMR Relaxation Time in Unconventional Shale Hydrocarbon Resources" Society of Petrophysicists and Well Log Analysts 53rd Annual Logging Symposium, 2012, pp. 1-9 (nine (9) pages).

Zandavi S. H. et al. "Characterization of the Pore Structures and Surface Properties of Shale using the Zeta Adsorption Isotherm Approach" Energy & Fuels, 2015, pp. 3004-3010, vol. 29, American Chemical Society (seven (7) pages).

Lowry et al. "Effect of Surface Chemistry on Confined Phase Behavior in Nanoporous Media: An Experimental and Molecular Modeling Study" Langmuir, 2018, pp. 9349-9358, vol. 34, American Chemical Society (ten (10) pages).

Barsotti E. et al. "Solution Gas Drive in Tight Oil Reservoirs: New Insights from Capillary Condensation and Evaporation Experiments" Unconventional Resources Technology Conference, 2018, pp. 1-9 (nine (9) pages).

Barsotti E. et al. "Phenomenological Study of Confined Criticality: Insights from the Capillary Condensation of Propane, n-Butane, and n-Pentane in Nanopores" Langmuir, 2018, pp. 4473-4483, vol. 34, American Chemical Society (11 pages).

Barsotti E. et al. "Capillary Condensation of Binary and Ternary Mixtures of n-Pentane-Isopentane-C $O_2$ in Nanopores: An Experimental Study on the Effects of Composition and Equilibrium" Langmuir, 2018, 1967-1980, vol. 34, American Chemical Society (14 pages).

VTI-SA+ "Specifications," 2009, TA Instruments (six (6) pages).

VTI-SA+ "Designed for High Performance Sorption Analysis of Materials Under Controlled Conditions of Temperature and Humidity", 2018, TA Instruments, http://www.tainstruments.com/vti-sa/ (23 pages).

IsoSORP Sorption Analysis Under Extreme Conditions "Modular Design can be configured to match Specific Requirements of your Applications", 2018, TA Instruments, http://www.tainstruments.com/isosorp/ (51 pages).

* cited by examiner

NANOCONDENSATION APPARATUS

FIELD OF THE INVENTION

The present invention relates to a nanocondensation apparatus for studying interactions between fluids and solids and to methods for studying these interactions.

BACKGROUND

Interactions between fluids and solids can be studied by recording the mass and/or composition of a fluid as a function of time. In the fields of adsorption and capillary condensation, a method wherein the mass of the fluid indicates the phase of the fluid is broadly termed as "gravimetric."

Gravimetric apparatuses are superior to other methods of measurement because they use high-precision balances to measure the mass of a fluid in real time. The use of high-precision balances negates the possibility of incurring errors through equation-of-state mass calculations, which are inherent to other methods, and allows for an understanding of the kinetics of adsorption, desorption, and capillary condensation. Furthermore, gravimetric apparatuses may be compatible with extreme temperatures and pressures and may be used for flow-through measurements, capabilities that are extremely difficult, if not impossible, to achieve with other types of apparatuses.

Apparatuses that study adsorption, desorption, and capillary condensation by using the gravimetric method are known in the art, and commercial gravimetric apparatuses can be purchased from vendors. These apparatuses and their use in gravimetric methods are described in Gor et al., 2013; Russo, Ribeiro Carrott, & Carrott, 2012; Russo et al., 2012; Qiao, Bhatia, & Nicholson, 2004; Shim, Lee, & Moon, 2006; http://www.rubotherm.com/rubotherm-gmbh-en.html The apparatuses known in the art are not geared towards the petroleum industry. These apparatuses use microbalances or magnetic suspension balances, can only accommodate small solid substance quantities (i.e., a few milligrams to a few grams), and cannot accommodate a true core holder. As such, measurements of reservoir fluids in reservoir cores at reservoir conditions cannot be performed using the apparatuses known in the art.

SUMMARY OF THE INVENTION

The present invention provides a nanocondensation apparatus comprising at least one mass comparator, at least one core holder, an environmental chamber, and a pump. The present invention also provides methods for studying a fluid-solid system comprising measuring changes in mass of a fluid present in an adsorbent with the nanocondensation apparatus.

DETAILED DESCRIPTION OF THE INVENTION

Figure 1A:
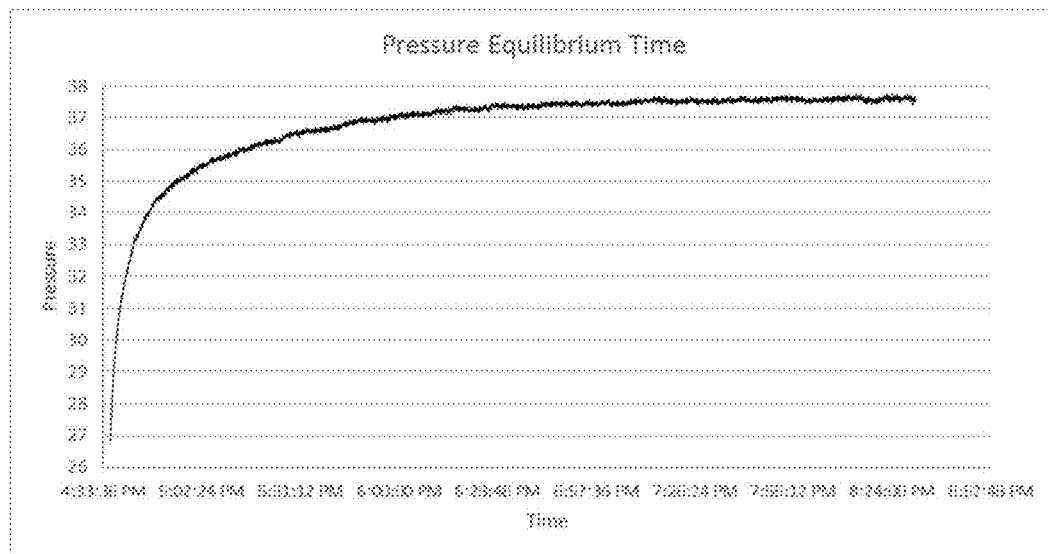
FIG. 1A. Sample pressure transducer reading from the environmental chamber of the nanocondensation apparatus. Readings vary from fluid to fluid. Readings also vary depending on whether adsorption or desorption is taking place.
Figure 1B:
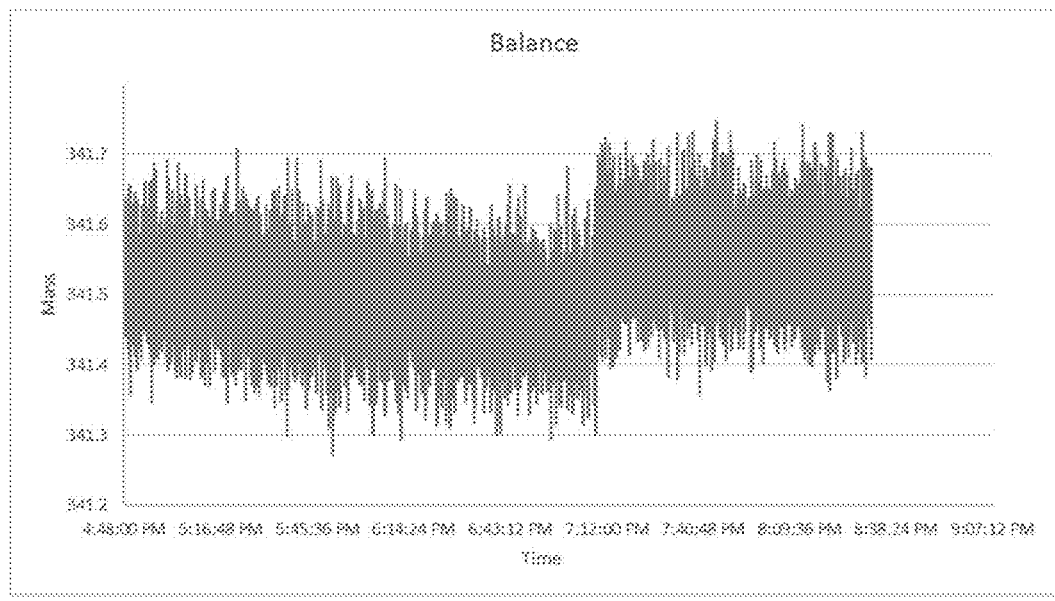
FIG. 1B. Sample mass reading from the mass comparator of the nanocondensation apparatus. Readings vary from fluid to fluid. Readings also vary depending on whether adsorption or desorption is taking place.

The present invention provides a nanocondensation apparatus comprising a mass comparator, a core holder, an environmental chamber, and a pump.

One embodiment of the invention is a nanocondensation apparatus wherein the mass comparator is a high capacity mass comparator.

A further embodiment of the invention is a nanocondensation apparatus wherein the mass comparator is a Mettler Toledo XPE505C mass comparator.

A further embodiment of the invention is a nanocondensation apparatus wherein the mass comparator is housed outside the environmental chamber.

A further embodiment of the invention is a nanocondensation apparatus wherein a hook or insulated wire is attached to a bottom surface of the mass comparator.

A further embodiment of the invention is a nanocondensation apparatus wherein the hook or insulated wire hangs inside the environmental chamber.

A further embodiment of the invention is a nanocondensation apparatus wherein the core holder hangs from the hook or insulated wire.

A further embodiment of the invention is a nanocondensation apparatus wherein the core holder is selected from:

a core holder comprising a body, endcaps, a hanging plate filters, compression fittings, and a modified compression spring;

a core holder comprising a body, endcaps, a hanging plate filters, compression fittings, a modified compression spring, and a flexible cylinder encapsulated inside the body of the core holder;

a core holder comprising a body, endcaps, a hanging plate filters, compression fittings, a modified compression spring, and spacers attached to the endcaps; and a core holder comprising a body, endcaps, a hanging plate filters, compression fittings, a modified compression spring, a sleeve on the outside of the core body, and a hand crank on the surface of the sleeve.

A further embodiment of the invention is a nanocondensation apparatus wherein the environmental chamber is a Thermotron XSE-600-3-3-MS environmental chamber.

A further embodiment of the invention is a nanocondensation apparatus wherein the environmental chamber has an operating temperature range of −100° C. to 232° C.

A further embodiment of the invention is a nanocondensation apparatus wherein the operating pressure ranges from vacuum to 10,000 psi.

A further embodiment of the invention is a nanocondensation apparatus wherein the environmental chamber interfaces with at least four resistance temperature detectors and at least two thermocouples.

A further embodiment of the invention is a nanocondensation apparatus wherein the environmental chamber comprises ports on the sides of the chamber and on top of the chamber.

A further embodiment of the invention is a nanocondensation apparatus wherein the environmental chamber comprises a draft shield.

A further embodiment of the invention is a nanocondensation apparatus wherein the pump is housed outside the environmental chamber.

A further embodiment of the invention is a nanocondensation apparatus wherein the pump is a hydrocarbon-free turbo-molecular pump.

A further embodiment of the invention is a nanocondensation apparatus wherein the pump is a dual cylinder Q6000 Quizix pump.

A further embodiment of the invention is a nanocondensation apparatus wherein the pump is housed inside the environmental chamber.

Pumps that may be housed inside the environmental chamber include dual cylinder Q5000 Quizix Pumps.

A further embodiment of the invention is a nanocondensation apparatus further comprising a gas chromatograph.

A further embodiment of the invention is a nanocondensation apparatus wherein the gas chromatograph is an Agilent 7890B gas chromatograph.

A further embodiment of the invention is a nanocondensation apparatus wherein the gas chromatograph is customized to be capable of Detailed Hydrocarbon Analysis.

A further embodiment of the invention is a nanocondensation apparatus wherein the gas chromatograph is customized to be capable of Simulated Distillation.

A further embodiment of the invention is a nanocondensation apparatus wherein the gas chromatograph is customized to be capable of analyzing fixed gases.

A further A further embodiment of the invention is a nanocondensation apparatus wherein the gas chromatograph measures the composition of bulk fluid and the composition of confined fluid.

A further embodiment of the invention is a nanocondensation apparatus wherein the gas chromatograph is made out of a highly corrosion-resistant metal alloy.

A further embodiment of the invention is a nanocondensation apparatus wherein the gas chromatograph is fitted with a high-pressure gas inlet valve.

A further embodiment of the invention is a nanocondensation apparatus wherein the gas chromatograph is fitted with heated tubing and/or a heated gas inlet valve.

A further embodiment of the invention is a nanocondensation apparatus comprising more than one mass comparator and more than one core holder.

A further embodiment of the invention is a nanocondensation apparatus comprising more than one mass comparator and more than one core holder, wherein the number of core holders is the same as the number of mass comparators.

A further embodiment of the invention is a nanocondensation apparatus comprising more than one mass comparator and more than one core holder, wherein each core holder is connected to one of the mass comparators via a hook or insulated wire.

A further embodiment of the invention is a nanocondensation apparatus comprising between 2 and 10 mass comparators and between 2 and 10 core holders.

A further embodiment of the invention is a nanocondensation apparatus comprising 4 mass comparators and 4 core holders.

A further embodiment of the invention is a nanocondensation comprising more than one mass comparator and more than one core holder, wherein the core holders are selected from the group consisting of:

a core holder comprising a body, endcaps, a hanging plate filters, compression fittings, and a modified compression spring;

a core holder comprising a body, endcaps, a hanging plate filters, compression fittings, a modified compression spring, and a flexible cylinder encapsulated inside the body of the core holder;

a core holder comprising a body, endcaps, a hanging plate filters, compression fittings, a modified compression spring, and spacers attached to the endcaps; and a core holder comprising a body, endcaps, a hanging plate filters, compression fittings, a modified compression spring, a sleeve on the outside of the core body, and a hand crank on the surface of the sleeve.

A further embodiment of the invention is a nanocondensation apparatus comprising more than one mass comparator and more than one core holder, wherein the core holders are all the same type of core holder.

A further embodiment of the invention is a nanocondensation apparatus comprising more than one mass comparator and more than one core holder, wherein the core holders are different types of core holder.

Figure 9:
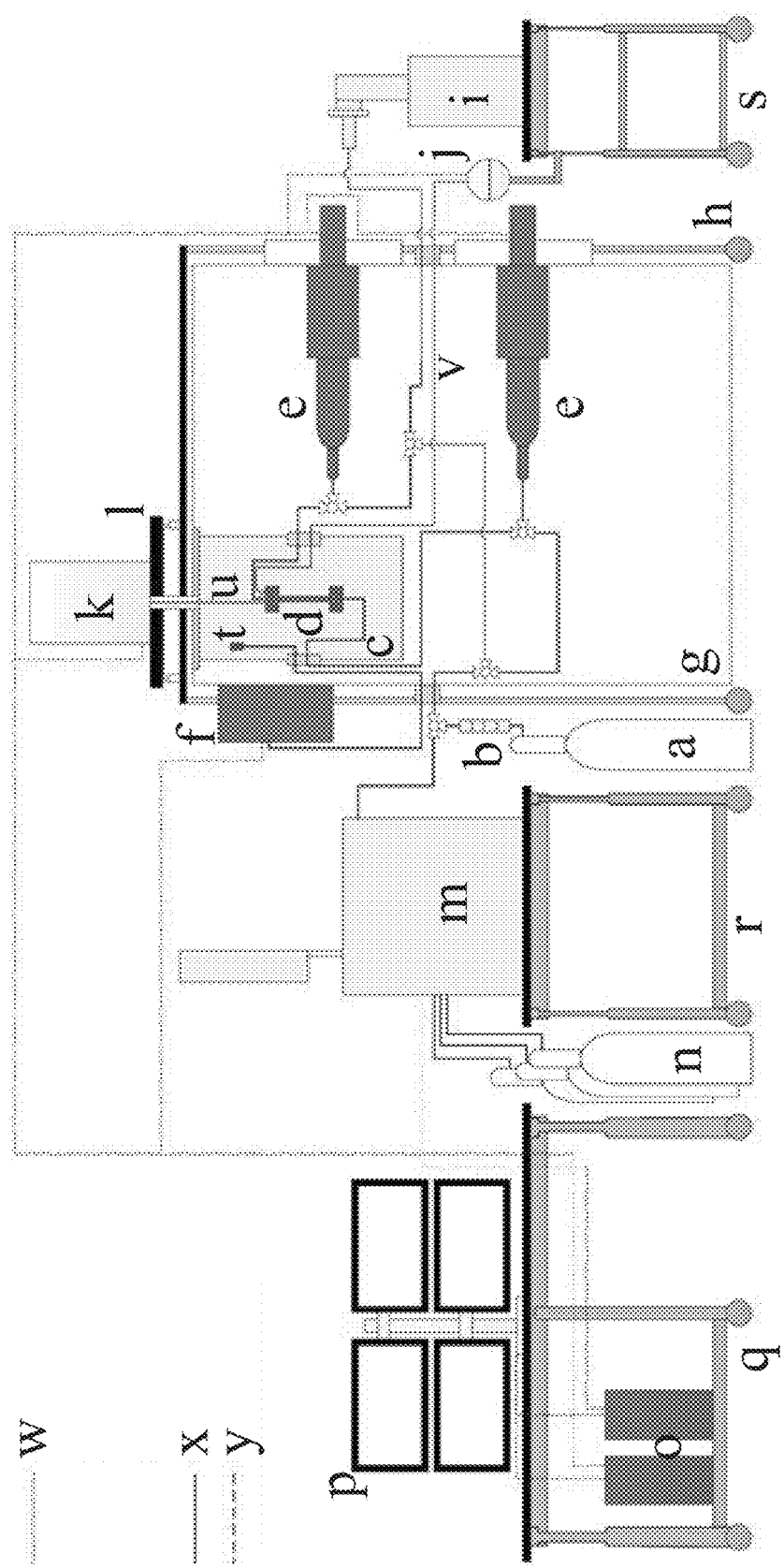
FIG. 9. Nanocondensation apparatus.

The nanocondensation apparatus of the invention maintains a variety of fluids at specific temperatures (e.g., temperatures in a range from −100° C. to 232° C.) and pressures (e.g., pressures in a range from vacuum to 10,000 psi). In addition, the nanocondensation apparatus has the ability to simulate overburden pressure. Consequently, the nanocondensation apparatus of the invention may be used to study interactions between fluids and solids, including adsorption, desorption, and nanocondensation (also known as "capillary condensation"). In particular, the nanocondensation apparatus may be used to re-create reservoir conditions during capillary condensation measurements. Further, the nanocondensation apparatus may be used to achieve the temperatures and pressures necessary to study single-component fluids in a variety of adsorbent pore types. FIG. 9 shows a setup for the nanocondensation apparatus.

An important part of any gravimetric apparatus is the balance used to measure the amount of fluid adsorbed or desorbed. The nanocondensation apparatus of the invention requires high resolution and a large maximum load to study capillary condensation at reservoir conditions. Accordingly, a mass comparator (k) is used in the nanocondensation apparatus instead of a traditional balance, as traditional balances have insufficient capacity and resolution. Unlike traditional balances, mass comparators weigh by difference, allowing for high resolution with large maximum loads. For example, the Mettler Toledo XPE505C mass comparator has a resolution of 0.01 milligrams even at its maximum load of 520 grams. As shown in FIG. 9, the mass comparator may be placed on top of an anti-vibration table (l).

The nanocondensation apparatus of the invention can accommodate an entire core and core holder (d) with a mass of up to the maximum load of the mass comparator used in the nanocondensation apparatus. For example, if the nanocondensation apparatus uses a Mettler Toledo XPE505C mass comparator, the nanocondensation apparatus can accommodate an entire core and core holder with a mass of up 520 g.

Use of a high capacity mass comparator makes it possible to introduce fluid to the core holder via flexible lines (v) and to allow for the forced flow of fluids through the core holder.

As a result, investigations of both single-component and multicomponent fluids in both static and flow-through measurements can be conducted.

Mass comparators have a specific window of operating temperatures. For example, the minimum and maximum operating temperatures of the Mettler Toledo XPE505C mass comparator are 10° C. and 30° C., respectively. Accordingly, precautions are taken to protect the mass comparator's sensitive electronics in experiments carried out at extreme conditions (e.g., reservoir temperatures and reservoir pressures). These precautions include placing the mass comparator on top of an environmental chamber (g) while hanging an adsorbent inside the environmental chamber from a hook or insulated wire (u) on the bottom of the mass comparator. The precautions also include containing experimental pressures within high pressure, high temperature tubing (x) and the core holder, which houses the adsorbent.

An environmental chamber (e.g., Thermotron XSE-600-3-3-MS) is used to ensure precise temperature control of the nanocondensation apparatus. The environmental chamber may be customized to include an extended lower operating temperature of −100° C., an extended upper operating temperature of 232° C., the capacity to interface with four or more resistance temperature detectors (RTDs) and two or more thermocouples, and ports on both the sides and on top of the chamber. Including ports on both the sides and on top of the chamber may be useful to pass lines and wires into and out of the chamber, including the wire suspending the core holder from the mass comparator. For example, thermocouple and/or RTD wires (t) may be inside the environmental chamber and the thermocouple and/or RTD box (f) may be placed outside the environmental chamber. The ports may also be useful to anchor a homemade draft shield (c), which may be fastened around the core holder to prevent air currents in the chamber from impairing the resolution of the mass comparator.

In addition, the environmental chamber may be purged with an inert gas (e.g., gaseous nitrogen). Purging the environmental chamber with an inert gas increases the safety of high-pressure, high-temperature reservoir condition experiments. Also, purging the environmental chamber with an inert gas helps prevent ice formation during low temperature experiments. The inert gas may be stored in a gas cylinder (a) outside of the environmental chamber and filtered through a gas dryer (b) prior to entering the environmental chamber.

A pump (e) (e.g., a dual cylinder Q6000 Quizix pump, which has a maximum pressure of 10,000 psi) is used in the nanocondensation apparatus to pressurize fluids under study. If the pump has a high maximum operating temperature, it is housed outside of the environmental chamber. For example, the dual cylinder Q6000 Quizix pump has a maximum operating temperature of 160° C. and was housed outside of the environmental chamber. Other pumps may have lower or higher maximum operating temperatures and may be housed either outside or inside of the environmental chamber.

In static experiments, both cylinders of the Quizix pump were simply used to pressurize fluids.

In experiments requiring the injection of pre-heated fluids, heating tape may be used to heat the cylinders of the Quizix pump. The use of heating tape serves as an alternative to housing the cylinders of the Quizix pump inside of the environmental chamber.

A hydrocarbon-free turbo-molecular pump (i) may be used in the nanocondensation apparatus to vacuum out the system and de-gas the adsorbent. A hydrocarbon-free turbo-molecular pump has magnetic bearings instead of oil-lubricated bearings. Consequently, lubricant fumes do not adsorb to tubing during vacuuming. Hydrocarbon-free turbo-molecular pump can achieve vacuum levels of at least $10^{-6}$ mbar.

Three types of core holders may be used in the nanocondensation apparatus. The core holders in the nanocondensation apparatus may be used like any core holder in petroleum engineering research: they can sustain high pressure, high temperature reservoir condition experiments, and may be modified for the application of overburden stress.

Figure 2:
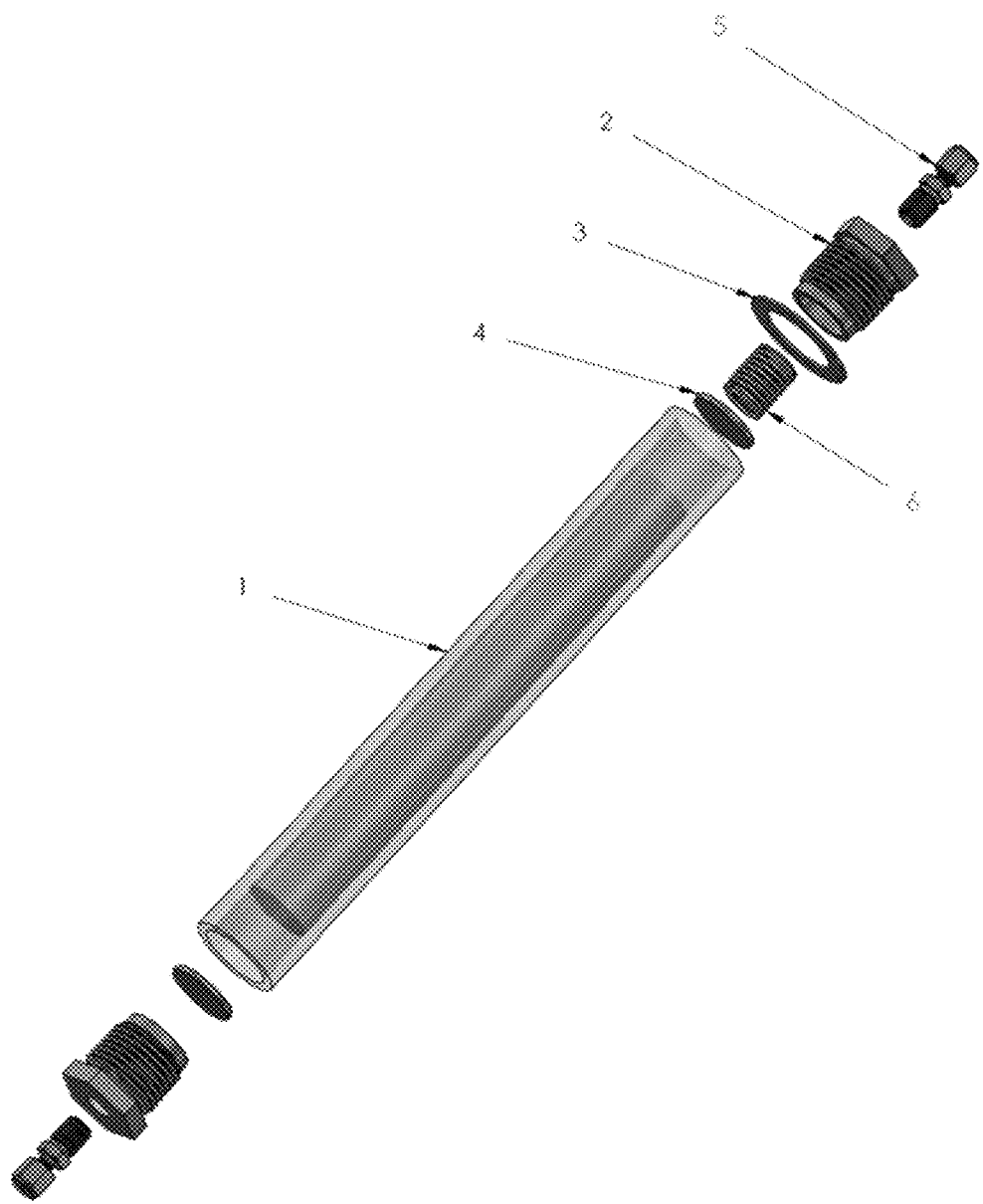
FIG. 2. Core holder.

The first type of core may be used for initial studies of simple fluids in ideal adsorbents. FIG. 2 shows a first type of core holder. The first type of core holder comprises a body (1), endcaps (2), a hanging plate (3), filters (4), compression fittings (5), and a modified compression spring (6).

Figure 3:
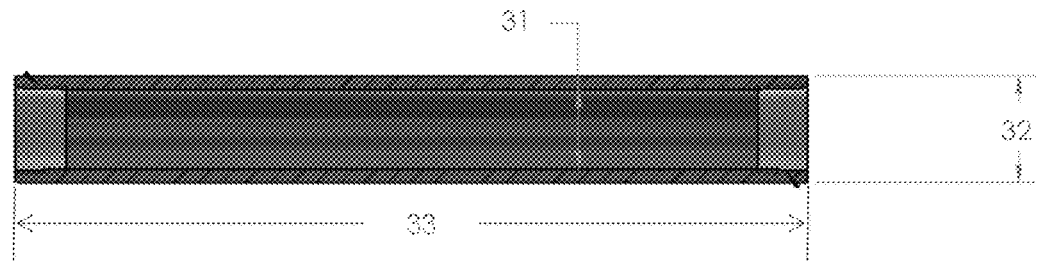
FIG. 3. Detail of core holder body.

FIG. 3 illustrates a core holder body. The core holder body may be made out of titanium, stainless steel, or carbon fiber. It can have an internal diameter (31) in the range of 0.1-2 in., an external diameter (32) in the range of 0.1-2 in., and a length (33) in the range of 4-10 in. The internal diameter is preferably in the range of 0.5-1.5 in., the external diameter is preferably in the range of 0.5-1.5 in., and the length is preferably in the range of 4-7 in. As an example, a core holder may have an internal diameter of 0.75 in., an external diameter of 1.0 in., and a length of 4 in. The core holder body shown in FIG. 3 may serve as the core holder body for the first, second, third, and fourth type of core holders.

Figure 4:
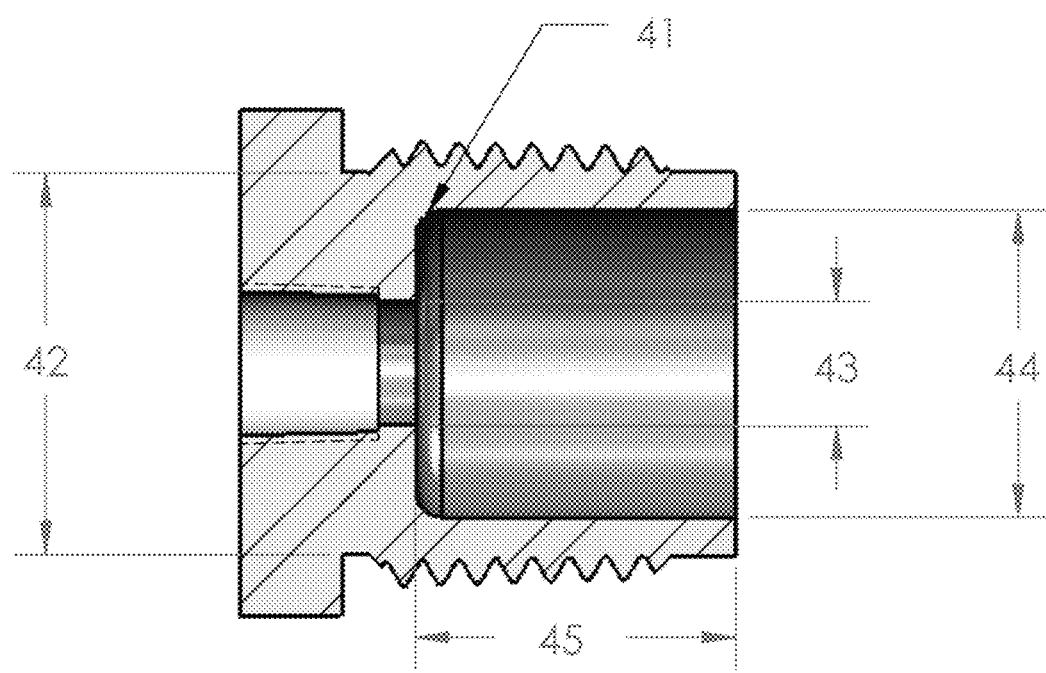
FIG. 4. Detail of core holder endcap.

FIG. 4 shows an endcap that may serve as an endcap for the first, second, third, and fourth type of core holders. Endcaps may be made out of titanium or stainless steel. For the endcaps of the first, second, third, and fourth types of core holder, the curvature of the internal diameter (41) may be in the range of 0-0.05 in., the external diameter (42) may be in the range of 0.1-2 in., the diameter of the port for the compression fitting (43) may be in the range of 0.015-0.5 in., the internal diameter (44) may be in the range of 0.1-2 in., and the length of the thread (45) may be in the range of 0.5-3 in.

For the first, second, third, and fourth type of core holders, the curvature of the internal diameter is preferably in the range of 0-0.03 in., the external diameter is preferably in the range of 0.5-1.5 in., the diameter of the port for the compression fitting is preferably in the range of 0.05-0.25 in., the internal diameter is preferably in the range of 0.5-1.5 in., and the length of the thread is preferably in the range of 0.5-1.5 in.

Alternatively, for the third type of core holder, the curvature of the internal diameter is preferably in the range of 0-0.03 in., the external diameter is preferably in the range of 0.5-1.5 in., the diameter of the port for the compression fitting is preferably in the range of 0.05-0.25 in., the internal diameter is preferably in the range of 0.5-1.5 in., and the length of the thread is preferably in the range of 1-3 in.

As an example, an endcap may have a curvature of the internal diameter of the endcap of 0.03 in., an external diameter of 0.746 in., a diameter of the port for the compression fitting of 0.242 in., an internal diameter of 0.600 in., and a length of the thread of 0.625 in.

As another example, an endcap may have a curvature of the internal diameter of the endcap of 0.03 in., an external diameter of 0.746 in., a diameter of the port for the compression fitting of 0.242 in., an internal diameter of 0.600 in., and a length of the thread of 2 in.

Figure 5A:
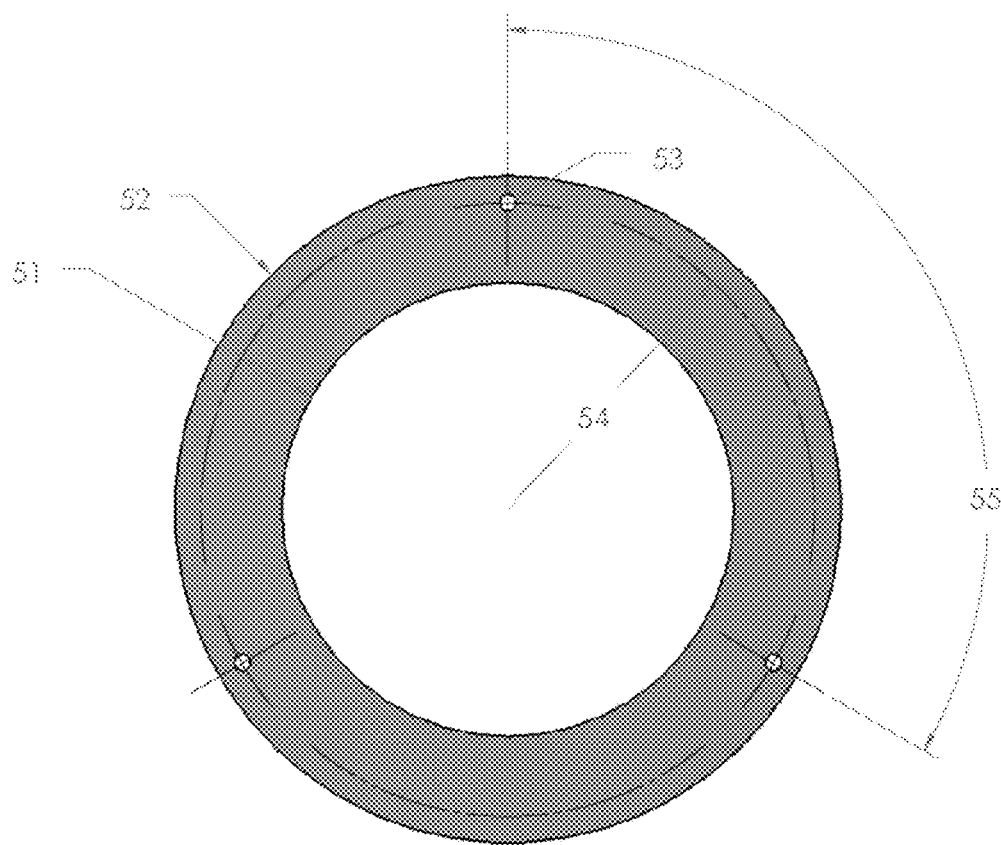
FIG. 5A. Schematic detail of core holder hanging plate.
Figure 5B:
FIG. 5B. Schematic detail of core holder hanging plate.

FIGS. 5A and 5B show a schematic of a hanging plate. Hanging plates may be made out of titanium, stainless steel, or aluminum. Preferably, hanging plates are made out of aluminum. A hanging plate may have an internal diameter (51) in the range of 0.1-2 in., an external diameter (52) in the range of 0.1-3 in., and a thickness (56) in the range of 0.1-1 in. A hanging plate may have at least three holes (53) through which hanging cables may be inserted. The holes may be evenly spaced, e.g., each of three holes has a distance (55) of 120° between itself and the two other holes. The holes may be placed at a radius from the center of the hanging plate (54) in the range of 0.05-1.5 in.

Preferably, a hanging plate has an internal diameter in the range of 0.5-2.0 in., an external diameter in the range of 0.5-2.0 in., and a thickness in the range of 0.025-1 in. Preferably, the holes are placed at a radius from the center of the hanging plate in the range of 0.25-1 in. Most preferably, the thickness of the hanging plate is in the range of 0.375-1 in.

As an example, a hanging plate has an internal diameter of 0.850 in., an external diameter of 1.250 in., and a thickness of 0.035 in. As an example, the holes are placed at a radius from the center of the hanging plate of 0.575 in.

As another example, a hanging plate has an internal diameter of 0.850 in., an external diameter of 1.250 in., and a thickness of 0.50 in. As an example, the holes are placed at a radius from the center of the hanging plate of 0.575 in.

Figure 5C:
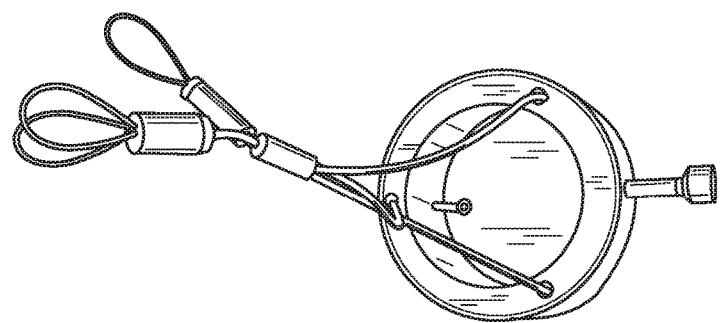
FIG. 5C. Core holder hanging plate.
Figure 5D:
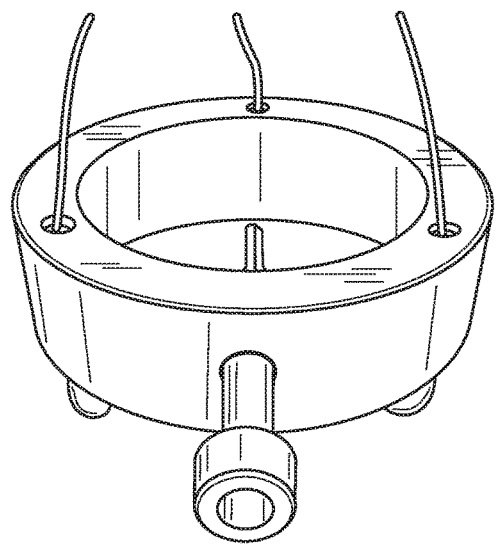
FIG. 5D. Core holder hanging plate.

FIGS. 5C and 5D show a photograph of a hanging plate with hanging cables inserted through the holes and a screw on the side of the hanging plate for tightening the hanging plate to the rest of the core holder. The screw may be a $\frac{7}{64}$-in. Allen screw or larger. In another embodiment, the hanging plate may comprise two or more screws on the side. The length of the hanging cables is in the range of 3-50 in. Preferably, the length of the hanging cables is in the range of 3-20 in. The hanging plates shown in FIGS. 5A, 5B, 5C, and 5D may serve as hanging plates for the first, second, third, and fourth type of core holders.

Figure 6:
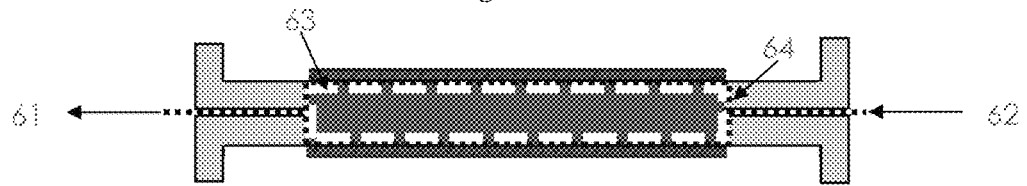
FIG. 6. Second type of core holder.

FIG. 6 shows a schematic of the second type of core holder. Like the first type of core holder, the second type of core holder comprises a body, endcaps, a hanging plate, filters, compression fittings, and a modified compression spring. The second type of core holder further comprises a flexible cylinder (63, thick white dashed line) encapsulated inside the body of the core holder. The second type of core holder tolerates high pressures (up to 10,000 psi), high temperatures (up to 232° C.), and the application of overburden stress and may be used for advanced experiments, including experiments on reservoir fluids and reservoir rocks (e.g., 1" core plugs, 1.5" core plugs, and crushed rock).

For example, the second type of core holder may be used in advanced studies of capillary condensation in the presence of overburden pressure. Overburden fluid (e.g., mineral oil) may be pumped into the void between the flexible cylinder and the body of the core holder to supply a confining pressure, simulating overburden. The path of the overburden fluid is shown as a thin black dotted line (64) in FIG. 6. The experimental fluid and overburden fluid inflow (62) and experimental fluid and overburden fluid outflow (61) are also shown in FIG. 6.

As another example, in flow-through experiments, one cylinder of the Quizix pump may control the pressure of fluids flowing into the second type of core holder, while the other cylinder of the Quizix pump may be used to provide back pressure.

Figure 7A:
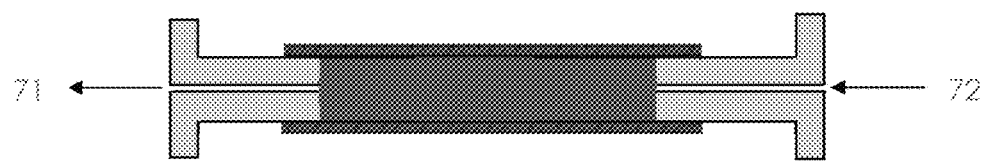
FIG. 7A. Third type of core holder, with no pressure applied.
Figure 7B:
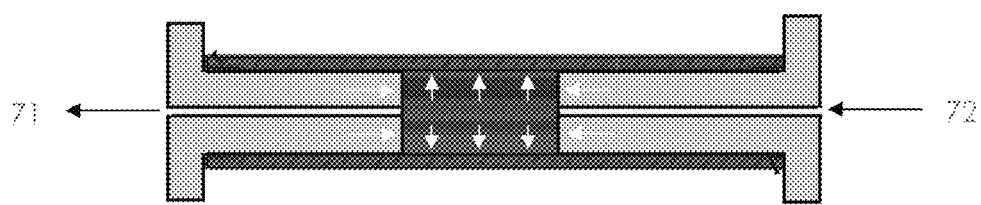
FIG. 7B. Third type of core holder, with pressure applied.

FIGS. 7A and 7B show schematics of the third type of core holder. This type of core holder may be used to apply overburden pressure by mechanical means. Like the first type of core holder, the third type of core holder comprises a body, endcaps, a hanging plate, filters, compression fittings, and a modified compression spring. The third type comprises either: endcaps (e.g., 0.5-1.5 in. in length) that are lengthened by attaching a spacer (e.g., 0.5-1.5 in. in length) to the endcap, such that the total length of the endcap+spacer combination is, e.g., 1-3 in; or long endcaps (e.g., 1-3 in). By tightening the encap+spacer combination or by tightening the long endcap, mechanical pressure is applied to the core.

FIG. 7A illustrates the third type of core holder when there is no pressure applied to the core, and FIG. 7B illustrates the third type of core holder when pressure is applied to the core. The application of pressure causes the core to shorten and widen, as indicated by the white arrows in FIG. 7B. Numbers 71 and 72 show the experimental fluid outflow and experimental fluid inflow, respectively.

Figure 8:
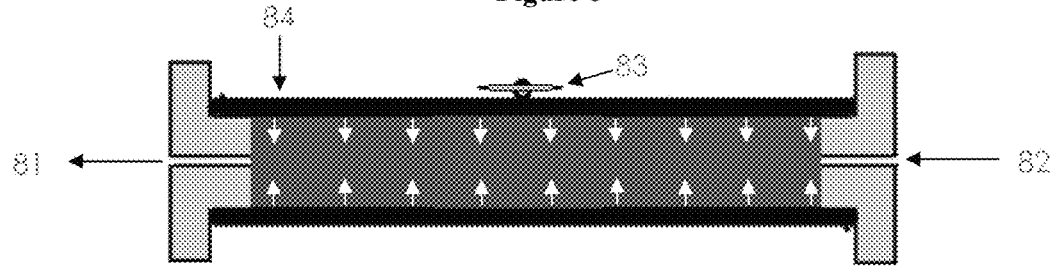
FIG. 8. Fourth type of core holder.

FIG. 8 shows the fourth type of core holder. This type of core holder may be used to apply overburden pressure by mechanical means. Like the first type of core holder, the fourth type of core holder comprises a body, endcaps, a hanging plate, filters, compression fittings, and a modified compression spring. The fourth type of core holder further comprises a sleeve (84) on the outside of the core body with a hand crank (83) on the surface of the sleeve. By turning the hand crank one way, the sleeve—and therefore the core body—constricts, causing pressure that squeezes the core. The pressure is illustrated by the white arrows in FIG. 8. Numbers 81 and 82 show the experimental fluid outflow and experimental fluid inflow, respectively.

A gas chromatograph (m in FIG. 9) (e.g., an Agilent 7890B) may be used in the nanocondensation apparatus to monitor the concentrations of fluids adsorbed and desorbed for the advanced study of multi-component fluids. The gas chromatograph may be customized to analyze all fluids encountered in capillary condensation experiments. For example, the gas chromatograph may be customized to be capable of Detailed Hydrocarbon Analysis to study hydrocarbon fluids. Further, the gas chromatograph may be customized to be capable of Simulated Distillation for crude oil. In addition, the gas chromatograph may be customized to be capable of analyzing fixed gases (e.g., nitrogen and carbon dioxide). The plumbing of the gas chromatograph may also be custom-made out of a highly corrosion-resistant metal alloy (e.g., Hastelloy) and may be fitted with high-pressure (e.g., 3000 psi) and/or heated gas inlet valve to ensure the proper analysis of reservoir fluids.

The gas chromatograph may also be used to measure the composition of bulk fluid and/or the composition of confined fluid. To measure the composition of confined fluid, a liquid nitrogen trap may be used to draw the confined fluid out of an adsorbent in the core holder. The confined fluid is collected from the liquid nitrogen trap and then is transferred to the gas chromatograph for analysis.

FIG. 9 further depicts a support structure (h) over the environmental chamber; a pressure gauge (j) (e.g., a Rosemount pressure gage) to monitor pressure; chromatographic gases (n), computers (o), monitors (p), to control the gas chromatograph and view experimental results; a workstation (q) for the computers and monitors; a chromatography bench (r) on which to place the gas chromatograph; a vacuum bench on which to place the vacuum (s); electrical wires (w); and a thermostat (y).

Figure 10:
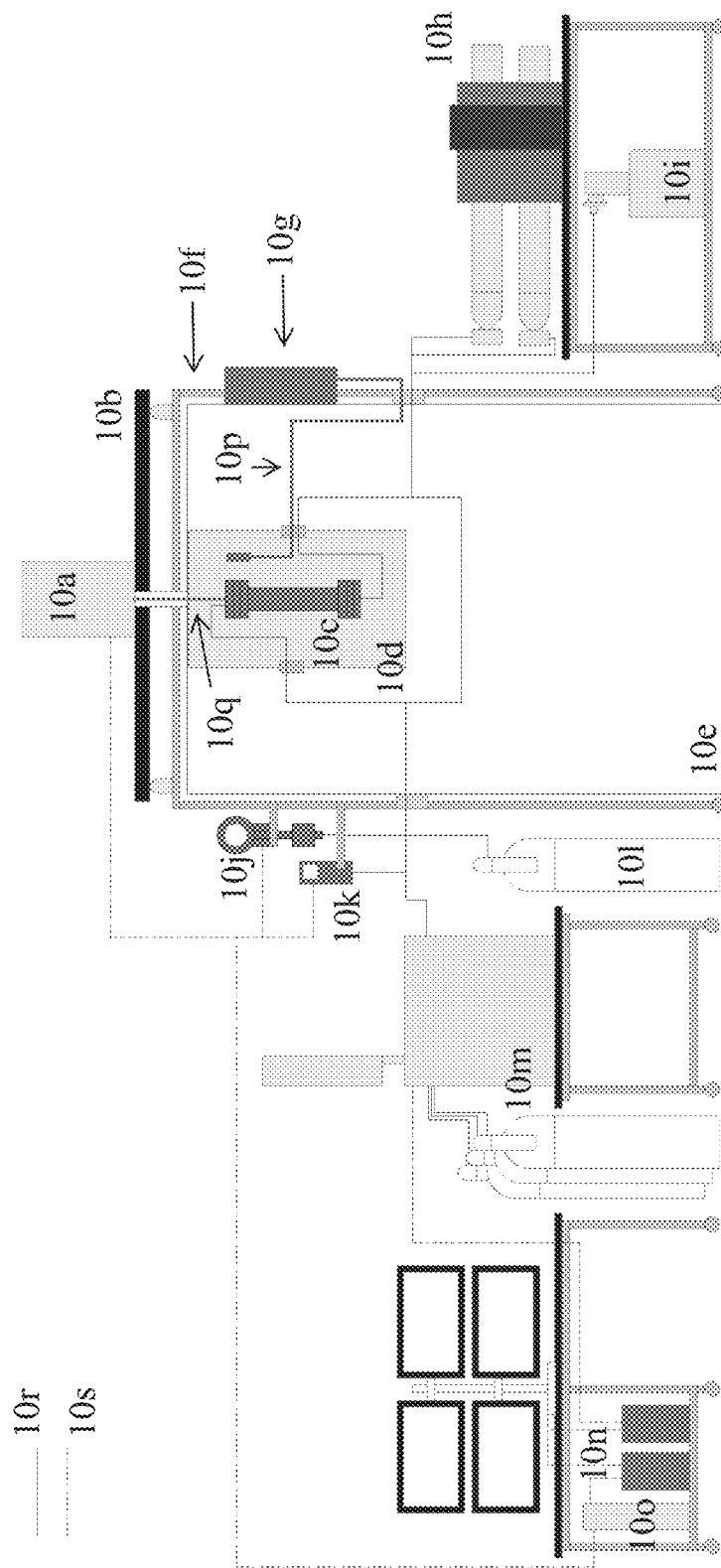
FIG. 10. Nanocondensation apparatus.

Another embodiment of the nanocondensation apparatus is shown in FIG. 10. The nanocondensation apparatus comprises a balance (10*a*), an anti-vibration table (10*b*), core holder (10*c*), a draft shield (10*d*), an environmental chamber (10*e*), a frame (10*f*), a thermocouple power supply and data logger (10*g*), a dual cylinder Quizix pump (10*h*), a turbomolecular pump (10*i*), a pressure transducer (10*j*), a vacuum gauge (10*k*), gas cylinders (10*l*) comprising inert gases, a gas chromatograph (10*m*), computers (10*n*), a data acquisition box (10*o*), a thermocouple wire (10*p*), an insulated wire (10*q*), gas lines (10*r*), and electrical wires (10*s*).

The present invention also provides methods for studying the interactions between fluids and solids.

One embodiment of the invention is a method of studying a fluid-solid system comprising measuring changes in mass of a fluid present in an adsorbent with a nanocondensation apparatus comprising a mass comparator, a core holder, an environmental chamber, and a pump, wherein:
  a) the adsorbent is placed in the core holder;
  b) a temperature and pressure are set; and
  c) changes in mass of the fluid are measured with the mass comparator.

Another embodiment of the invention is a method of studying a fluid-solid system, wherein the fluid is selected from the group consisting of at least one simple fluid and at least one reservoir fluid.

Another embodiment of the invention is a method of studying a fluid-solid system, wherein the adsorbent is selected from the group consisting of an ideal adsorbent and a reservoir core.

Another embodiment of the invention is a method of studying a fluid-solid system, wherein the fluid-solid system is at reservoir temperature and pressure conditions.

Another embodiment is a method of studying a fluid-solid system, wherein the fluid is injected continuously or stepwise into the adsorbent.

Another embodiment is a method of studying a fluid-solid system, wherein the fluid is injected with the pump or by hand into the adsorbent.

Another embodiment is a method of studying a fluid-solid system, wherein the temperature of the fluid-solid system is controlled by measuring the temperature with a thermocouple and adjusting the temperature of the nanocondensation apparatus.

Another embodiment is a method of studying a fluid-solid system, wherein the pressure and the mass of the fluid are measured over an equilibrium time at selected time intervals.

Another embodiment is a method of studying a fluid-solid system, wherein the equilibrium time is in a range of 0.5 seconds to 20,000 seconds.

Another embodiment is a method of studying a fluid-solid system, wherein the selected time intervals are averaged over a range of 0.1 to 100 seconds.

Another embodiment is a method of studying a fluid-solid system, wherein the selected time intervals are averaged over a range of 0.5 to 50 seconds.

Another embodiment is a method of studying a fluid-solid system, wherein the selected time intervals are averaged over a range of 1 to 10 seconds.

Another embodiment is a method of studying a fluid-solid system, wherein the pressures and masses measured at the selected time intervals are averaged over the equilibrium time.

Another embodiment of the invention is a method of studying more than one fluid-solid system simultaneously, comprising measuring changes in mass of a fluid present in more than one adsorbent with a nanocondensation apparatus comprising more than one mass comparator, more than one core holder, an environmental chamber, and a pump, wherein:
  a) an adsorbent is placed in each core holder;
  b) a temperature and pressure are set; and
  c) changes in mass of the fluid are measured with each mass comparator.

A further embodiment of the invention is a method of studying more than one fluid-solid system simultaneously, wherein the number of core holders is the same as the number of mass comparators.

A further embodiment of the invention is a method of studying more than one fluid-solid system simultaneously, wherein each core holder is connected to one of the mass comparators via a hook or insulated wire.

A further embodiment of the invention is a method of studying more than one fluid-solid system simultaneously, wherein the nanocondensation apparatus comprises between 2 and 10 mass comparators and between 2 and 10 core holders.

A further embodiment of the invention is a method of studying more than one fluid-solid system simultaneously, wherein the nanocondensation apparatus comprises 4 mass comparators and 4 core holders.

A further embodiment of the invention is a method of studying more than one fluid-solid system simultaneously, wherein between 2 and 10 measurements can be carried out simultaneously.

A further embodiment of the invention is a method of studying more than one fluid-solid system simultaneously, wherein 4 measurements can be carried out simultaneously.

Definitions

The term "fluid" refers to a liquid or a gas.

The term "simple fluid" means a single-component liquid or gas. Examples of simple fluids include $C_1$-$C_{20}$ alkanes (e.g., methane, ethane, propane, butane, isobutane, pentane, neopentane, hexane, heptane, octane, nonane, decane), $C_2$-$C_{20}$ alkenes, $C_2$-$C_{20}$ alkynes, $C_1$-$C_{20}$ alkanols (e.g., methanol, ethanol, isopropanol), $C_2$-$C_{20}$ alkenols, aromatic hydrocarbons (e.g., benzene, toluene), $C_3$-$C_{20}$ cycloalkanes (e.g., cyclopentane, cyclohexane, methylcyclohexane), $C_3$-$C_{20}$ cycloalkenes, water, nitrogen, carbon dioxide, and oxygen.

The term "reservoir fluid" refers to a fluid mixture found in a reservoir rock.

The term "ideal adsorbent" refers to an ordered nanoporous material.

The term "reservoir core" refers to a sample of reservoir rock, which is a type of nanoporous rock that contains oil, gas, brine, and or $CO_2$.

The term "reservoir temperature and pressure conditions" refers to conditions wherein the temperature and pressure reflect the temperature and pressure of reservoir rock. The temperature and pressure of the reservoir rock varies as a function of the reservoir rock's proximity to the earth's mantle and the composition of the porous medium of the reservoir rock. Reservoir temperatures and pressures can be determined by methods known in the art.

The term "ambient temperature and pressure conditions" refers to conditions wherein the temperature is room temperature and the pressure is atmospheric pressure. Room temperature ranges between 15° C. and 30° C., preferably between 18° C. and 27° C., and most preferably between 20° C. and 25° C. Atmospheric pressure ranges between 750 and 1050 mbar. Preferably, atmospheric pressure is about 1013 mbar.

The term "vacuum" refers to reduced pressures in the range of about $10^{-12}$ mbar to about 750 mbar.

The term "capillary condensation" refers to the process by which a fluid in vapor phase adsorbs into a porous medium, builds multiple layers of the adsorbed vapor phase through inter-molecular forces, and at a threshold temperature and pressure nucleates into a condensed phase that fills the pores of the porous medium.

The term "bulk fluid" refers to fluid that is confined in pores equal to or greater than 100 nm.

The term "confined fluid" refers to fluid that is confined in pores smaller than 100 nm.

EXAMPLES

Example 1

Isothermal Capillary Condensation Experiments

In capillary condensation experiments, the core holder is first filled with an adsorbent sample and hung inside the environmental chamber from a hook or insulated wire on the bottom of the mass comparator via an insulated wire.

Next, the core holder and tubing of the apparatus are subjected to high vacuum and a temperature of approximately 100° C. to degas any vapors in the system.

Once degassing is finished, the temperature of the environmental chamber is set to a desired experimental temperature ("$T_{exp}$").

To study fluid adsorption, a fluid is injected into the core holder at a desired experimental pressure ("$P_1$") by the Quizix pump. Constant temperature and pressure are maintained until fluid adsorption is complete (i.e., until no changes in the mass or the pressure of the fluid are observed).

Several adsorption measurements can be taken in sequence. Alternatively, an adsorption measurement can be taken, and, once adsorption is complete, a desorption measurement can be taken.

To study fluid desorption, the mass and pressure of the adsorbed fluid are measured. Constant temperature and pressure are maintained until desorption of the fluid is complete (i.e., until no changes in the mass or the pressure of the fluid are observed).

Once desorption is finished, the temperature of the environmental chamber is set to $T_{exp}$ again, the pressure is increased to a new desired pressure ("$P_2$"), and the fluid is injected again until adsorption is complete.

Several desorption measurements can be taken in sequence. Alternatively, a desorption measurement can be taken, and, once desorption is complete, an adsorption measurement can be taken.

These adsorption and desorption steps are repeated, at constant temperature and different pressures, as many times as desired. In particular, the adsorption and desorption steps are repeated until a full adsorption isotherm (i.e., a plot of fluid amount adsorbed against pressure) is created.

Completion of adsorption is evidenced by constant mass and pressure readings for an extended period of time. Similarly, completion of desorption is evidenced by constant mass and pressure readings for an extended period of time. Mass readings are taken from the mass comparator, and pressure readings are taken from pressure transducers or vacuum gauges that are located outside of the environmental chamber.

If the adsorption/desorption processes did not exhibit hysteresis, the desorption pressure was the same as the pressure of adsorption.

If the adsorption/desorption process exhibited hysteresis, the desorption pressure was greater than the pressure of adsorption.

Example 2

Isobaric Capillary Condensation Experiments

In capillary condensation experiments, the core holder is first filled with an adsorbent sample and hung inside the environmental chamber from a hook or insulated wire on the bottom of the mass comparator via an insulated wire.

Next, the core holder and tubing of the apparatus are subjected to high vacuum and a temperature of approximately 100° C. to degas any vapors in the system.

Once degassing is finished, the pressure of the environmental chamber is set to a desired experimental temperature ("$P_{exp}$").

To study fluid adsorption, a fluid is injected into the core holder at a desired experimental temperature ("$T_1$"). The temperature is set using the environmental chamber, which uses feedback from a thermocouple or RTD. Constant temperature and pressure are maintained until fluid adsorption is complete (i.e., until no changes in the mass or the temperature of the fluid are observed).

Several adsorption measurements can be taken in sequence. Alternatively, an adsorption measurement can be taken, and, once adsorption is complete, a desorption measurement can be taken.

To study fluid desorption, the mass and temperature of the adsorbed fluid are measured. Constant temperature and pressure are maintained until desorption of the fluid is complete (i.e., until no changes in the mass or the temperature of the fluid are observed).

Once desorption is finished, the pressure of the environmental chamber is set to $P_{exp}$ again, the temperature is increased to a new desired temperature ("$T_2$"), and the fluid is injected again until adsorption is complete.

Several desorption measurements can be taken in sequence. Alternatively, a desorption measurement can be taken, and, once desorption is complete, an adsorption measurement can be taken.

These adsorption and desorption steps are repeated, at constant pressure and different temperatures, as many times as desired. In particular, the adsorption and desorption steps are repeated until a full adsorption isobaric plot (i.e., a plot of fluid amount adsorbed against temperature) is created.

Completion of adsorption is evidenced by constant mass and temperature readings for an extended period of time. Similarly, completion of desorption is evidenced by constant mass and temperature readings for an extended period of time. Mass readings are taken from the mass comparator, and temperature readings are taken with at least one thermometer housed inside the environmental chamber.

The time starting with adsorption or desorption and extending to a constant mass and temperature or to a constant mass and pressure reading is called the "equilibrium time."

Example 3

Use of the Nanocondensation Apparatus

The systems are leak tested to ensure none of the permanent metal tubing leaks under pressure or vacuum. The tubing should always be tested under pressure first, then under vacuum.

Installation of the core holder comprises: (1) connecting the core holder to the rest of the nanocondensation apparatus, (2) leak testing the core holder, and (3) outgassing the system.

If the pressure of the fluid at room temperature is well above (e.g., at least 100 psi) the saturation pressure of the fluid at the experimental temperature, the fluid may be injected without a Quizix pump.

If the pressure of the fluid at room temperature is not well above (e.g., at least 100 psi) the saturation pressure of the fluid at the experimental temperature, the fluid is injected with a Quizix pump.

If the fluid is a mixture, the mixture is analyzed with the chromatograph at specific time intervals.

The foregoing description and examples have been set forth merely to illustrate the invention and are not meant to be limiting. Since modifications of the described embodiments incorporating the spirit and the substance of the invention may occur to persons skilled in the art, the invention should be construed to include all variations within the scope of the claims and equivalents thereof.

The invention claimed is:

1. A nanocondensation apparatus comprising:
   (a) an environmental chamber;
   (b) a mass comparator, wherein the mass comparator sits above the environmental chamber;
   (c) a hook or insulated wire, wherein the hook or insulated wire hangs inside the environmental chamber and is attached to a bottom surface of the mass comparator;
   (d) a core holder, wherein the core holder hangs inside the environmental chamber from the hook or insulated wire; and
   (e) a pump, wherein the pump may be housed inside the environmental chamber or outside the environmental chamber.

2. The nanocondensation apparatus of claim 1, wherein the mass comparator is a high capacity mass comparator.

3. The nanocondensation apparatus of claim 1, wherein the mass comparator is housed outside the environmental chamber.

4. The nanocondensation apparatus of claim 1, wherein the core holder is selected from:
   (1) a core holder comprising a body, endcaps, a hanging plate filters, compression fittings, and a modified compression spring;
   (2) a core holder comprising a body, endcaps, a hanging plate filters, compression fittings, a modified compression spring, and a flexible cylinder encapsulated inside the body of the core holder;
   (3) a core holder comprising a body, endcaps, a hanging plate filters, compression fittings, a modified compression spring, and spacers attached to the endcaps; and
   (4) a core holder comprising a body, endcaps, a hanging plate filters, compression fittings, a modified compression spring, a sleeve on the outside of the core body, and a hand crank on the surface of the sleeve.

5. The nanocondensation apparatus of claim 1, wherein the environmental chamber has an operating temperature range of $-100°$ C. to $232°$ C.

6. The nanocondensation apparatus of claim 1, the operating pressure ranges from vacuum to 10,000 psi.

7. The nanocondensation apparatus of claim 1, wherein the pump is housed outside the environmental chamber.

8. The nanocondensation apparatus of claim 1, wherein the pump is a hydrocarbon-free turbo-molecular pump.

9. The nanocondensation apparatus of claim 1, further comprising a gas chromatograph.

10. The nanocondensation apparatus of claim 1, further comprising between 1 and 9 additional mass comparators and between 1 and 9 additional core holders.

11. A method of studying more than one fluid-solid system comprising measuring changes in mass of a fluid present in more than one adsorbent with the nanocondensation apparatus of claim 10, wherein:
    a) an adsorbent is placed in each core holder;
    b) a temperature and pressure are set; and
    c) changes in mass of the fluid are measured with each mass comparator,
    wherein temperature is set to a desired experimental temperature between $-100°$ C. and $232°$ C. using the environmental chamber, and
    wherein pressure is set to a desired experimental pressure between vacuum and 10,000 psi using the pump.

12. A method of studying a fluid-solid system comprising measuring changes in mass of a fluid present in an adsorbent with the nanocondensation apparatus of claim 1, wherein:
    a) the adsorbent is placed in the core holder;
    b) a temperature and pressure are set; and
    c) changes in mass of the fluid are measured with the mass comparator,
    wherein temperature is set to a desired experimental temperature between $-100°$ C. and $232°$ C. using the environmental chamber, and
    wherein pressure is set to a desired experimental pressure between vacuum and 10,000 psi using the pump.

13. The method of claim 12, wherein the fluid is selected from the group consisting of at least one simple fluid and at least one reservoir fluid.

14. The method of claim 12, wherein the adsorbent is selected from the group consisting of an ideal adsorbent and a reservoir core.

15. The method of claim 12, wherein the fluid-solid system is at reservoir temperature and pressure conditions.

16. The method of claim 12, wherein the pressure and the mass of the fluid are measured over an equilibrium time at selected time intervals.

17. The method of claim 12, wherein the pressures and masses measured at the selected time intervals are averaged over the equilibrium time.

18. The method of claim 12, wherein the temperature and the mass of the fluid are measured over an equilibrium time at selected time intervals.

19. The method of claim 12, wherein the temperatures and masses measured at the selected time intervals are averaged over the equilibrium time.

* * * * *